(12) United States Patent
Sintorn et al.

(10) Patent No.: US 11,002,689 B2
(45) Date of Patent: *May 11, 2021

(54) METHOD FOR QUANTIFICATION OF PURITY OF SUB-VISIBLE PARTICLE SAMPLES

(71) Applicant: Intelligent Virus Imaging Inc., Southern Pines, NC (US)

(72) Inventors: Ida-Maria Sintorn, Sollentuna (SE); Martin Ryner, Huddinge (SE); Gustaf Kylberg, Sollentuna (SE); Josefina Nilsson, Saktsjöbaden (SE)

(73) Assignee: INTELLIGENT VIRUS IMAGING INC., Southern Pines, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/549,603

(22) Filed: Aug. 23, 2019

(65) Prior Publication Data

US 2019/0376910 A1  Dec. 12, 2019

Related U.S. Application Data

(63) Continuation of application No. 16/068,232, filed as application No. PCT/US2017/050962 on Sep. 11, 2017, now Pat. No. 10,451,566.

(Continued)

(51) Int. Cl.
| | | |
|---|---|---|
| *G01N 23/04* | (2018.01) | |
| *G01B 21/28* | (2006.01) | |
| *C12Q 1/70* | (2006.01) | |
| *G06K 9/00* | (2006.01) | |
| *G01N 15/14* | (2006.01) | |

(Continued)

(52) U.S. Cl.
CPC .............. *G01N 23/04* (2013.01); *C12Q 1/70* (2013.01); *G01B 15/00* (2013.01); *G01B 21/28* (2013.01); *G01N 15/10* (2013.01); *G01N 15/1475* (2013.01); *G06K 9/00127* (2013.01); *G06K 9/00147* (2013.01); *G06K 9/4604* (2013.01); *G01N 2015/0038* (2013.01);

(Continued)

(58) Field of Classification Search
CPC .... G01N 23/04; G01N 15/10; G01N 15/1475; G01N 2015/0038; G01N 2015/1006; G01N 2015/1093; G01N 2223/401; G01N 2223/405; C12Q 1/70; G01B 15/00; G01B 21/28; G06K 9/00127
See application file for complete search history.

(56) References Cited

U.S. PATENT DOCUMENTS 10,451,566 B2 * 10/2019 Sintorn .................. G01N 23/04

* cited by examiner

Primary Examiner — Nicole M Ippolito
Assistant Examiner — Hanway Chang
(74) Attorney, Agent, or Firm — Fasth Law Offices; Rolf Fasth (57) ABSTRACT

The method is for quantification of purity of sub-visible particle samples. A sample to be analyzed is place in an electron microscope to obtain an electron microscopy image of the sample. The sample contains objects. The objects that have sizes being different from a size range of primary particles and sizes being within the size range of primary particles are enhanced. The objects are detected as being primary particles or debris. The detected primary particles are excluded from the objects so that the objects contain debris but no primary particles. A first total area (T1) of the detected debris is measured. A second total area (T2) of the detected primary particles is measured.

8 Claims, 7 Drawing Sheets

Related U.S. Application Data

(60) Provisional application No. 62/402,003, filed on Sep. 30, 2016.

(51) Int. Cl.
*G06K 9/46* (2006.01)
*G01B 15/00* (2006.01)
*G01N 15/10* (2006.01)
*G01N 15/00* (2006.01)

(52) U.S. Cl.
CPC ............ *G01N 2015/1006* (2013.01); *G01N 2015/1093* (2013.01); *G01N 2223/401* (2013.01); *G01N 2223/405* (2013.01)

METHOD FOR QUANTIFICATION OF PURITY OF SUB-VISIBLE PARTICLE SAMPLES

PRIOR APPLICATIONS

This application is a continuation patent application that claims priority from U.S. national phase application Ser. No. 16/068,232, filed 5 Jul. 2018, that claims priority from International Application No. PCT/US17/50962, filed 11 Sep. 2017, claiming priority from U.S. Provisional Patent Application No. 62/402,003, filed 30 Sep. 2016.

TECHNICAL FIELD

The present invention relates to a method for assessing and quantitatively measuring how pure a sample is by using electron microscopy.

BACKGROUND AND SUMMARY OF THE INVENTION

Developing and producing biopharmaceuticals typically involve several purification steps where cell debris, broken particles, other contaminants and clusters etc. should be removed so that the final product contains only the desirable primary particles. The purity and dispersion of the primary particles of interest (i.e. non-clustered primary particles) in the final product is important for its quality and efficacy. To quantitatively asses the purity is hence of importance for the final product but also during the upstream development and production processes to evaluate the efficacy and effect of each purification step. Electron microscopy is a method by which sub-visible particles can be imaged at a resolution sufficient to identifying the particles of interest (primary particles) as well as undesirable debris, contaminants and clusters in the sample. An objective quantitative measure of how pure a sample of sub-visible particles such as virus particles, virus-like particles, inorganic beads and other nanoparticles and micro-particles from liquid samples is important in many processes. For example, modified virus vectors are commonly used in gene therapy applications and modified virus particles are used as vaccines. However, the currently available methods for quantitatively assessing the purity are not very accurate and often involve manual steps that may distort the final result. There is a need for a more effective and reliable method to assess and measure the purity of liquid samples that contain sub-visible primary particles and contaminants/debris.

The method of the present invention provides a solution to the above-outlined problems. More particularly, the method is for quantification of purity of sub-visible particle samples. A sample to be analyzed is placed in an electron microscope to obtain an electron microscopy image of the sample. The sample contains objects of primary particles as well as debris. Debris could be broken or parts (sub-units) of primary particles, and/or contaminants, and/or primary particle or debris clusters or aggregates, and or left-over material from the production phase. The objects in the image are enhanced and have sizes that are different from a size range of primary particles and sizes that are within the size range of primary particles. The objects in the image are detected as being primary particles or debris. The detected primary particles are excluded from the remaining objects so that the objects detected as debris contain only debris and no primary particles. A first total area (T1) of the detected debris is measured. A second total area (T2) of the detected primary particles is measured. A ratio of the first total area (T1) to the second total area (T2) is calculated to determine a quantitative measurement of purity of the sample.

In another embodiment, the edges of objects in the image are enhanced and the objects have a size that is substantially similar to a size range of primary particles. A roundness of the objects is analyzed to identify primary particles.

In another embodiment, objects in the image that have a shape that is substantially similar to that of primary particles are identified as primary particles.

In another embodiment, the edges of objects in the image are enhanced and the objects have a size that is substantially similar to a size range of primary particles and a radial density profile of the objects is analyzed to identify primary particles.

In yet another embodiment, the edges of objects in the image are enhanced and the objects have a size that is substantially similar to a size range of primary particles, and a signal-to-noise ratio at the border of the objects are analyzed by measuring an average intensity of an interior of the objects compared to an average intensity just outside the objects.

In another embodiment, the edges of objects in the image are enhanced and the objects have a size that is substantially similar to a size range of primary particles and a local contrast of the objects are measured by analyzing a sharpness of an outer edge of the objects.

In another embodiment, the edges of objects in the image are enhanced and the objects have a size that is substantially similar to a size range of primary particles and the structure of the objects is measured by means of texture analysis to identify primary particles.

In another embodiment, the structure of the objects in the image is measured by means of texture analysis and analyzed to identify primary particles.

In another embodiment, a sample that contains virus particles or virus-like particles is placed in the electron microscope.

In yet another embodiment, the image is filtered with two smoothing filters to create a first filtered image and a second filtered image and subtracting the first filtered image from the second filtered image.

DETAILED DESCRIPTION

The present invention describes a unique method for quantitatively measuring the purity of a sample containing sub-visible or nano-particles (that may, for example, have a size of about 100 nm) in solution based on an automatic and objective image analysis of electron microscopy images of the sample. The sample may, for example, be liquid, dissolved solid or powder samples.

Negative stain transmission electron microscopy images may be used. In general, the purity measure of the present invention is, preferably, the area ratio of primary particles to non-primary particles (including small debris as well as large debris clusters). The principle steps of the method of the present invention are:

1. Placing a sample to be analyzed in an electron microscope to obtain an electron microscopy image of the sample;
2. Enhancing edges (such as fine edges) of primary particles in the image that have a size that is typical for the primary particle;
3. Specifically detecting all primary particles in the image by using a method that is adapted to identify the particular primary particles;
4. Enhancing objects of sizes typical for debris clusters and contaminants in the image;
5. Detecting all the enhanced objects in step 4 by using e.g., a thresholding method.
6. Excluding (subtracting) the identified primary particles from the detected enhanced objects;
7. Measuring a total area of the detected and remaining debris clusters and contaminants from step 6;
8. Measuring a total area of the detected primary particles detected in step 3; and
9. Calculating a ratio of the area resulting from step 7 to the area resulting from step 8.

Figure 1:
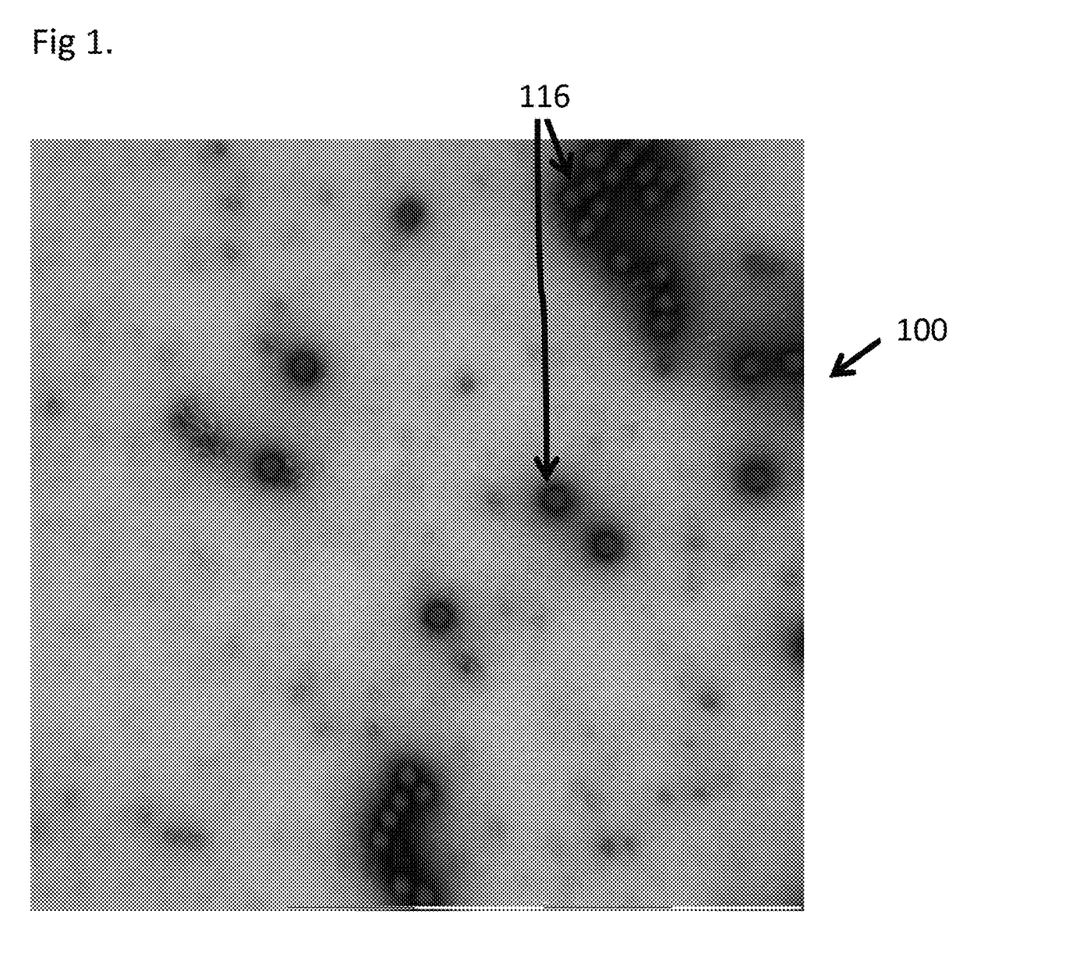
FIG. 1 is a transmission electron image of a negatively stained biological particle sample in solution.

A typical example image 100 is shown in FIG. 1, and steps 2-6 are illustrated in FIGS. 2-6. FIG. 7 shows the final result 102, i.e., the primary particles 120 and debris objects 106. The measured areas of the primary particles and debris objects, respectively, are used in steps 7-9 to derive the purity measure.

Figure 2:
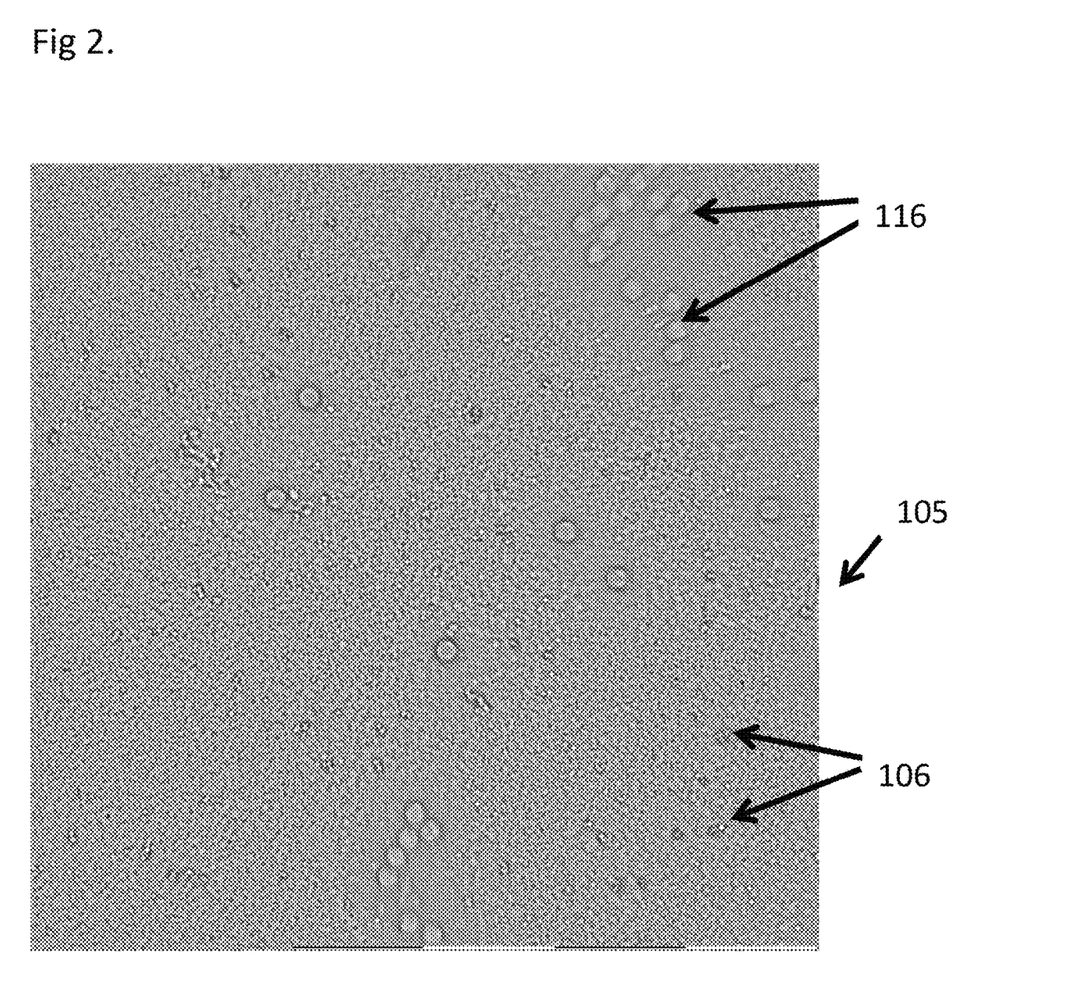
FIG. 2 is an image showing the result after the difference of Gaussians method has been used to enhance fine edges.

More particularly, FIG. 1 is a transmission electron microscopy image 100 of a negatively stained biological particle sample in solution. The biological particles may be virus particles or any other organic particles. Samples that contain inorganic particles may also be analyzed with the method of the present invention. A suitable method such as the difference of Gaussians or any other suitable method may be used to enhance, for example, the fine edges (or contrast/thin regions) of the objects 116 in the image that have a size that is typical for the primary particle (step 2) to be analyzed. FIG. 2 shows the result 105 after the difference of Gaussians method has been used to enhance the fine edges of the identified objects 116. The identified object 116 are mostly primary particles but may contain some undesirable debris and contaminants 106 (explained in more detail below). A certain type of virus particles may have an expected size of 100 nm so that particles that have a size that is substantially different are most likely not primary particles but undesirable debris particles 106 instead. It should be noted that the analysis in step 2 may not be limited to the size of the entire particles. It may also be possible to focus on parts of the structure of the primary particle that are specific to the desired primary particles such as the pattern of the particle or thickness of the outer edge. It is then possible to enhance a specific portion of the particle such as the pattern or the thickness of the outer edge of the particle.

The enhancement of fine edges of selected particles or primary particles (such as by using the difference of Gaussian) in the image has provided unexpected and surprisingly good results. For example, staining biological samples (such as virus particles) results in different amounts of stain surrounding the objects/particles in the image due to different thickness of the stain in different parts of the sample as well as around differently sized objects/particles. The amount (thickness) of the stain and hence where on the grid the purity measure is calculated directly influences the purity measure and may make the measurement less correct. As indicated above, edges or objects in a selected size range in the image are enhanced by using, for example, the difference of Gaussian approach. It is to be understood that other edge or object enhancing approaches may also be used. In the difference of Gaussians method, an image is filtered with two Gaussian smoothing filters (that have different smoothing factor sigma). One filtered image is then subtracted from the other which results in an image with enhanced edges or enhanced objects of, for example, a certain size. The result partly depends on the combination of smoothing factors used. It is on these modified images that the primary particles, debris and contaminants are then detected. As indicated above, the edge/object enhancing step reduces the effect of different amounts and uneven distribution of the stain. This important and innovative step is hence necessary in application/cases where uneven stain is a problem such as when analyzing biological samples of virus particles and other particles. In samples that only contain inorganic material/particles, the edge enhancing step may be excluded. In addition, enhancing objects (i.e. primary particles in steps 2/3) of a certain selected size or characteristic, such as edge thickness or pattern, prior to detecting all objects after enhancement according to step 4 (described below), reduces the problem of uneven background coloring and lighting in the image which otherwise could easily lead to false positioning of the object borders and even result in falsely or incorrectly missed or detected objects. In other words, the enhancement in step 2 makes it easier to identify the primary particles in view of the varied background colors and lighting from the microscope. For example, the enhancement removes or reduces the effect of lighter colors in certain segments of the image and the effect of gradients of intensity.

Figure 3:
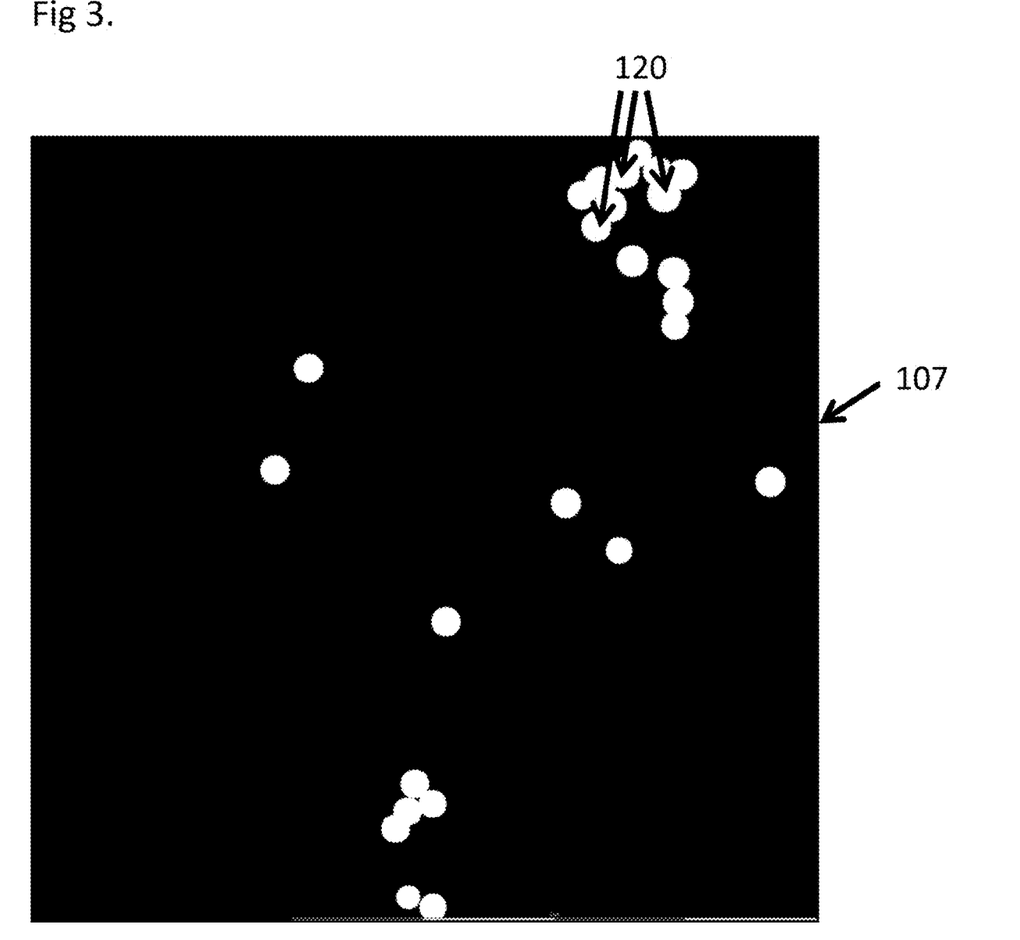
FIG. 3 is an image of primary objects detected in the image shown in FIG. 2 by using a specific detection method.

However, some of the undesirable debris and contamination particles may have a size that is similar to that of the primary particles to be analyzed. In other words, the enhancement in step 2 may enhance particles that happen to have a similar size or have other characteristics similar to primary particles but they are not primary particles. It is then necessary to further analyze the enhanced objects in step 2 by, for example, analyzing the shape or roundness of the objects 116 in order to identify and distinguish primary particles 120 from debris that may have sizes that are within the size range of the primary particles. This is done in step 3 (and the result 107 is shown in FIG. 3) that identifies (in white) the detected primary particles 120 by using a detection method such as analyzing the radial symmetry of the particles/objects identified in step 2 and as shown in FIG. 2.

In order to make the method of the present invention and the quantitative purity measure objective (i.e. user unbiased) and robust, the steps of the present method should preferably be performed automatically with user input only provided to select the approximate sizes of the primary particles as well as lower and upper limits of the non-primary particles/objects (debris and clusters). An important aspect of the present invention is the ability to automatically distinguish the primary particles from non-primary particles/objects. As indicated regarding step 3, circular primary particles (such as viral vectors) can, for example, be detected based on the circular symmetric characteristics or other methods that specifically detect the primary particles 120. For example, the radially symmetric virus particle structure may be transformed to a gray-level profile. It may be used to describe the structure by calculating the mean gray-level at each distance from the center going from the center and out towards a periphery or shell of the virus particle structure. It is also possible to develop mathematical algorithms to describe the virus particle structures or shape instead of relying on gray scale profiles.

An important feature of the method of the present invention is that it is possible to create templates based on the gray scale profiles to objectively describe the virus particles. The templates may be created by using mathematical methods also. In this way, all the detected objects in a size range may be compared to a profile or template that represent a typical primary particle and use the profile/template to determine if the detected object is sufficiently similar to the profile/template to be classified as a true primary particle 120. It may also be possible to use other methods in step 3 to identify the primary particles 120 such as methods to detect elliptical, rod-like or crystal-like shapes.

It is to be understood that the above reference to virus particles is merely an example and the present invention is not limited to virus particles. Also, the reference to the circularity/roundness of the particle is merely an example, and other characteristics such as specific patterns, specific shapes and object surfaces may also be used.

Regarding step 3 that is related to the specific detection of primary particles 120 (and to eliminate non-primary particles that have a size that is similar to primary particles), an additional step may be included, that uses the signal-to-noise ratio or local contrasts at the border of the objects 116. This is done to further improve the detection of primary particles 120 and the automatic decision about what is a primary particle or not. The signal-to-noise ratio is, preferably, measured as the average intensity in the interior of the particle compared to the average intensity just outside the particle. The local contrast approach may be used to analyze how sharp the outer and/or inner edges of the particle are to better be able to determine whether it is a primary particle or not. Also regarding step 3, for non-spherical particles, other methods designed for the detection of specific shapes or other characteristics of the primary particles 120, such as texture (pattern on the particle surface), can be used.

Figure 4:
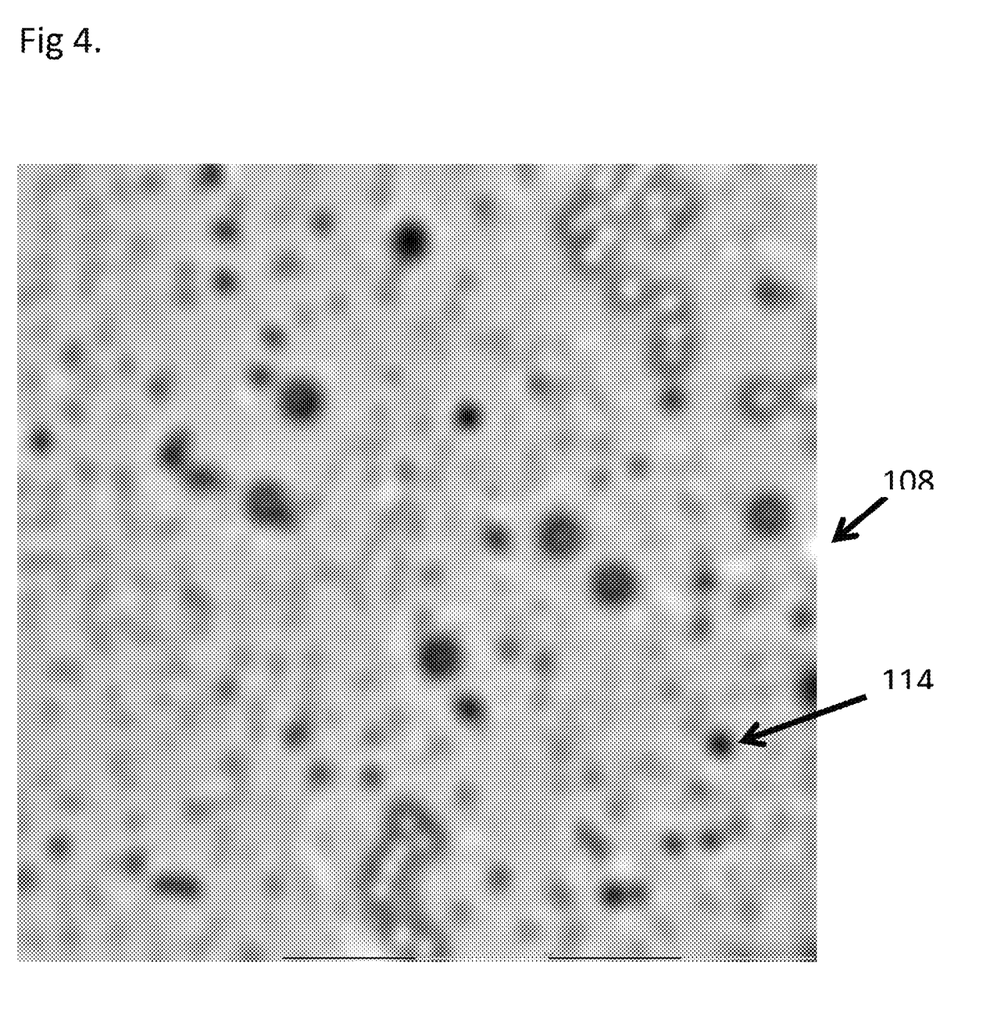
FIG. 4 is an image showing the result after enhancing objects of typical debris size using the difference of Gaussians method on the original image.

The next step is to detect undesirable debris and contaminants in the sample. FIG. 4 shows the result 108 after objects have been enhanced on the original image. One problem is that the analysis and enhancement in step 4 also identifies and includes some or all of the primary particles 120 identified in step 3. In step 4, all objects 114 in the image are enhanced by using, for example, the difference of Gaussians method. Debris and clusters can, for example, also be detected by an (automatic) intensity thresholding method such as Otsu's thresholding method. Manually choosing the intensity threshold would also work but it could easily introduce undesired user-bias.

Preferably, the objects 114 are identified by focusing on a certain size range that is typical for debris cluster and contaminants because debris/contaminants may have any shape and colors. It is possible to first focus on objects with sizes that are typical for debris and contaminants but smaller than primary particles and then focus on objects with sizes that are larger than primary particles. The intensity of the objects 114 is, preferably, analyzed to identify regions or areas that include debris and contaminants.

Figure 5:
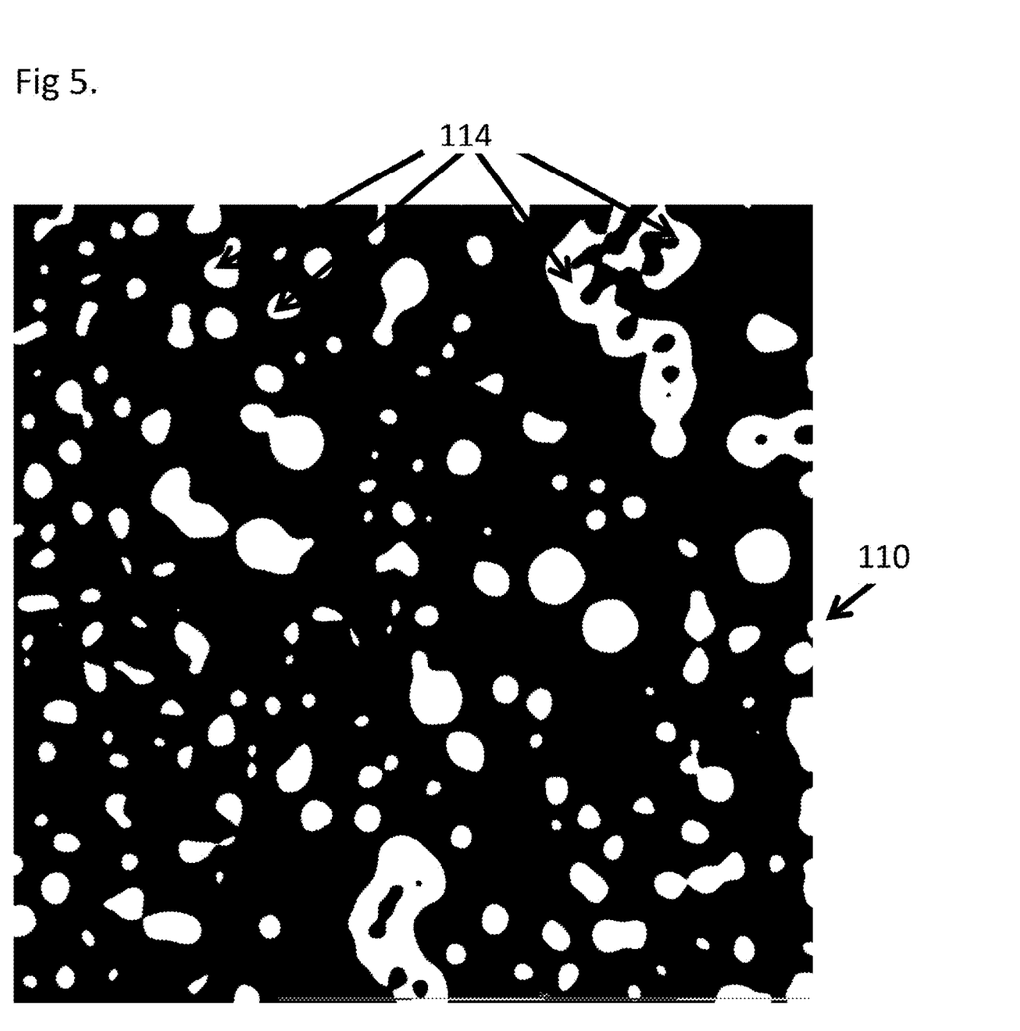
FIG. 5 is an image showing the result after thresholding the object-enhanced image.

In this way, all the enhanced objects 114 in the image are detected in step 5 and the result 110 is shown in FIG. 5. In other words, the identification method used in step 4 is not sufficiently specific to exclude the primary particles 120 so that both debris particles and some or all of the primary particles are identified as objects 114 and shown in result 110.

Figure 6:
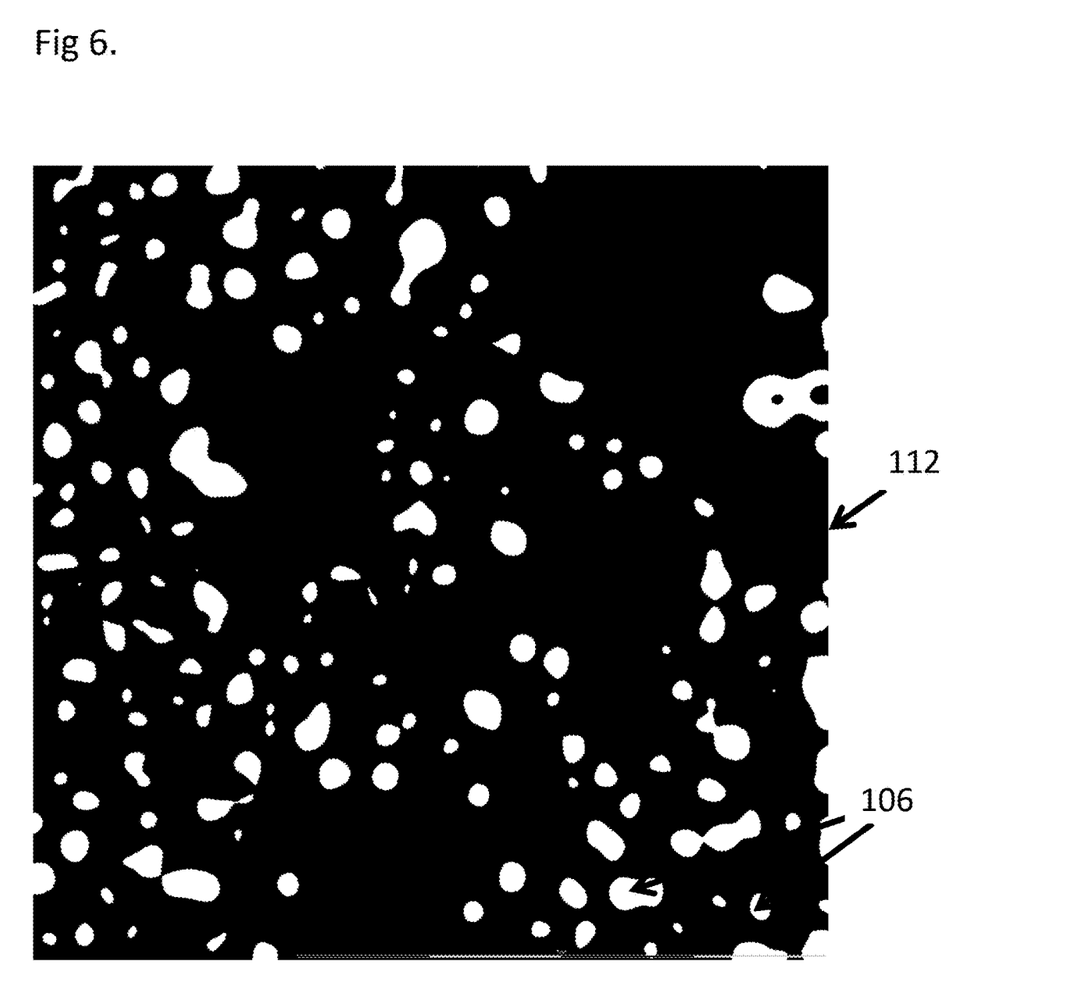
FIG. 6 is an image showing the result after removing objects corresponding to the primary particles.
Figure 7:
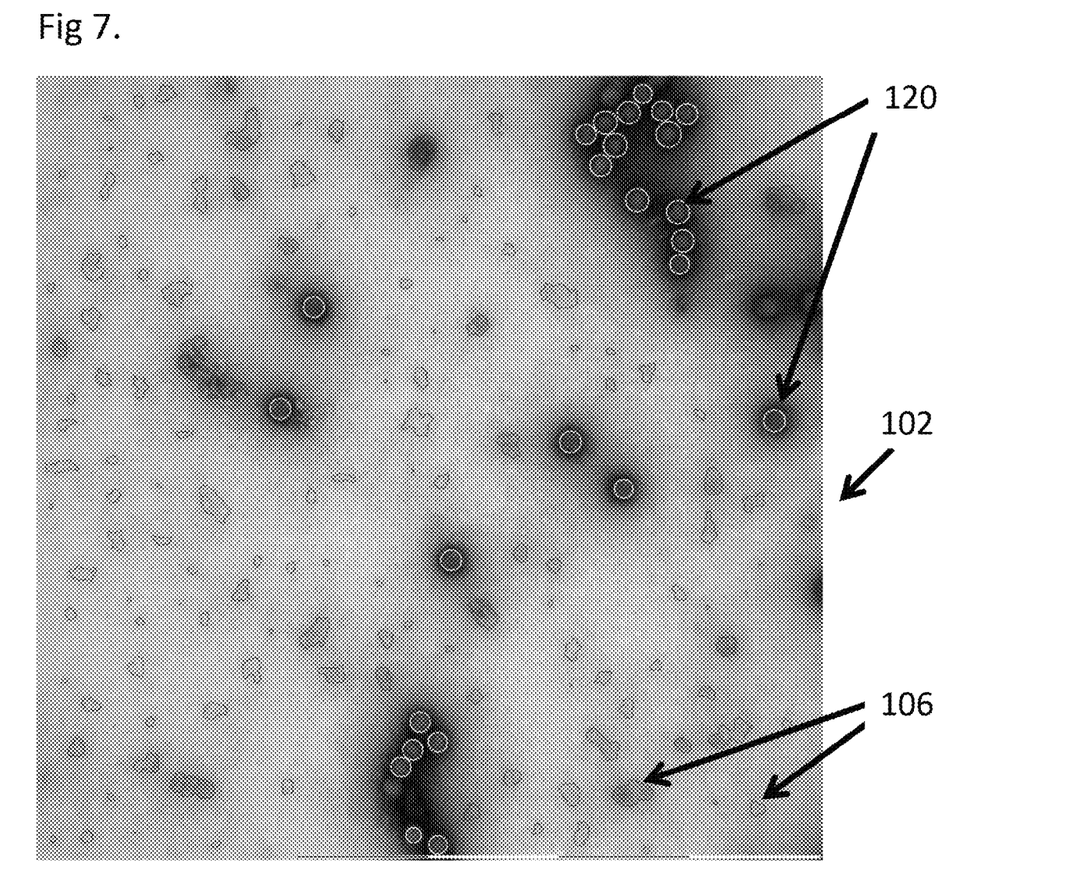
FIG. 7 is an image showing the final result including both primary particles and debris.

In step 6, the identified primary particles 120, as identified in step 3, that are also included in objects 114 are excluded or subtracted from the objects 114 shown in FIG. 5 so that only the detected debris and contaminants 106 are shown in result 112 in FIG. 6. This means any primary particles, that happened to have been included in objects 114 as a result of the enhancement method used in step 5, are removed so that result 112 only shows debris and contamination particles 106.

In step 7, the total area T1 of the remaining objects or debris 106 after step 6, i.e. after the primary particles have been removed, is measured. In step 8, the total area T2 of the detected primary particles 120, as shown in FIG. 3, is measured. In step 9, the ratio R of the areas resulting after step 7 and step 8, respectively, is calculated.

The described approach, quantifying purity as the area ratio of primary particles vs. other objects is robust. A few falsely detected or missed primary particles only affect the result in a nonsignificant way since the measurement is based on a large number of images that represent the sample well, preferably resulting from automated image acquisition (user unbiased) or manually acquired images.

While the present invention has been described in accordance with preferred compositions and embodiments, it is to be understood that certain substitutions and alterations may be made thereto without departing from the spirit and scope of the following claims.

We claim:

1. A method for quantification of purity of sub-visible particle samples, comprising:
    placing a sample in an electron microscope to obtain an electron microscopy image of the sample, the sample containing objects;
    detecting the objects in the image as being primary particles or debris;
    excluding the detected primary particles from the objects so that objects contain debris but no primary particles;
    measuring a first total area (T1) of the detected debris;
    measuring a second total area (T2) of the detected primary particles; and
    using the first total area (T1) and the second total area (T2) to determine a quantitative measurement of purity of the sample.

2. The method according to claim 1 wherein the method further comprises enhancing edges of objects in the image that have a size that is substantially similar to a size range of primary particles and analyzing a roundness of the objects to identify primary particles.

3. The method according to claim 1 wherein the method further comprises enhancing edges of objects in the image that have a size that is substantially similar to a size range of primary particles and analyzing a radial density profile of the objects to identify primary particles.

4. The method according to claim 1 wherein the method further comprises enhancing edges of objects in the image that have a size that is substantially similar to a size range of primary particles and analyzing a signal-to-noise ratio at the border of the objects by measuring an average intensity of an interior of the objects compared to an average intensity just outside the objects to identify primary particles.

5. The method according to claim 1 wherein the method further comprises enhancing edges of objects in the image that have a size that is substantially similar to a size range of primary particles and analyzing a local contrast of the objects by analyzing a sharpness of an edge of the objects to identify primary particles.

6. The method according to claim 1 wherein the method further comprises placing a sample that contains virus or virus-like particles in the electron microscope.

7. The method according to claim 1 wherein the method further comprises filtering the image with two smoothing filters to create a first filtered image and a second filtered image and subtracting the first filtered image from the second filtered image.

8. A method for quantification of purity of sub-visible particle samples, comprising:
   placing a sample in an electron microscope to obtain an electron microscopy image of the sample, the sample containing objects;
   enhancing the objects in the image having sizes being different from a size range of primary particles and sizes being within the size range of primary particles detecting the objects in the image as being primary particles or debris;
   excluding the detected primary particles from the objects so that objects contains debris but no primary particles;
   measuring a first total area (T1) of the detected debris;
   measuring a second total area (T2) of the detected primary particles; and
   calculating a ratio of the first total area (T1) to the second total area (T2) to determine a quantitative measurement of purity of the sample.

* * * * *